United States Patent
Stephenson et al.

(10) Patent No.: US 11,321,335 B2
(45) Date of Patent: May 3, 2022

(54) METHOD AND SYSTEM FOR SHARING ACCESS TO A DATABASE

(71) Applicant: DRUGDEV INC., Princeton, NJ (US)

(72) Inventors: Dimitrie Hugo Stephenson, Princeton, NJ (US); James Herschel Gryphon Shafer, Princeton, NJ (US); Melissa Jane Easy, Princeton, NJ (US)

(73) Assignee: DRUGDEV INC., Princeton, NJ (US)

( * ) Notice: Subject to any disclaimer, the term of this patent is extended or adjusted under 35 U.S.C. 154(b) by 391 days.

(21) Appl. No.: 16/286,125

(22) Filed: Feb. 26, 2019

(65) Prior Publication Data

US 2019/0197035 A1  Jun. 27, 2019

Related U.S. Application Data

(62) Division of application No. 14/399,421, filed as application No. PCT/US2013/040005 on May 7, 2013, now Pat. No. 10,255,332.

(Continued)

(51) Int. Cl.
*G06F 7/00* (2006.01)
*G06F 16/248* (2019.01)
(Continued)

(52) U.S. Cl.
CPC ...... *G06F 16/248* (2019.01); *G06F 16/24553* (2019.01); *G16H 10/20* (2018.01); *F04C 2270/041* (2013.01); *G16H 10/60* (2018.01)

(58) Field of Classification Search
CPC .............. G06F 16/248; G06F 16/9538; G06F 16/24556; G06F 16/355; G06F 16/40; G06F 16/532
See application file for complete search history.

(56) References Cited

U.S. PATENT DOCUMENTS

| | | | | |
|---|---|---|---|---|
| 6,143,898 A | * | 11/2000 | Etzbach | B41M 5/385 546/270.7 |
| 7,266,545 B2 | * | 9/2007 | Bergman | G06F 16/532 707/706 |

(Continued)

FOREIGN PATENT DOCUMENTS

| | | |
|---|---|---|
| WO | 03/015342 A1 | 2/2003 |
| WO | WO03015342 A1 * | 2/2003 |

(Continued)

OTHER PUBLICATIONS

Robust reading competitions: entries, results and future directions; Lucas et al; ICDAR 2003.*

(Continued)

*Primary Examiner* — Daniel A Kuddus
(74) *Attorney, Agent, or Firm* — John Maldjian; Jonathan B. David; Stevens & Lee PC

(57) ABSTRACT

A computer-implemented method for sharing access to a database of records relating to clinical trial investigators amongst a number of users is disclosed. Each record includes a number of data fields associated with a clinical trial investigator and has associated metadata indicating a record owner. The method comprises: a) receiving a database query from a first user; b) resolving the query using a first subset of the records in the database including only those records for which the associated metadata indicates that the record owner is the first user and those records for which the associated metadata indicates that the record owner is another user which has registered a sharing rule in respect of the first user, whereby the first user is granted permission to access its records; and c) generating a result set including only those records used to resolve the query that satisfy the query.

18 Claims, 4 Drawing Sheets

Related U.S. Application Data

(60) Provisional application No. 61/643,898, filed on May 7, 2012.

(51) Int. Cl.
*G16H 10/20* (2018.01)
*G06F 16/2455* (2019.01)
*G16H 10/60* (2018.01)

(56) References Cited

U.S. PATENT DOCUMENTS

| | | | |
|---|---|---|---|
| 7,356,840 B1* | 4/2008 | Bedell | G06F 21/6227 |
| | | | 726/13 |
| 7,627,550 B1* | 12/2009 | Adams | G06F 16/24556 |
| 8,024,327 B2* | 9/2011 | Tunkelang | G06F 16/245 |
| | | | 707/722 |
| 8,874,549 B2* | 10/2014 | Tunkelang | G06F 16/245 |
| | | | 707/722 |
| 9,135,337 B2* | 9/2015 | Venkataraman | H04N 21/482 |
| 2003/0033300 A1* | 2/2003 | Bergman | G06F 16/532 |
| 2003/0140043 A1* | 7/2003 | Hotchkiss | G16H 10/20 |
| 2005/0004994 A1 | 1/2005 | Chevallier et al. | |
| 2005/0055380 A1 | 3/2005 | Thompson | |
| 2005/0055381 A1 | 3/2005 | Ganesh | |
| 2005/0228817 A1 | 10/2005 | Hochberg | |
| 2005/0240354 A1* | 10/2005 | Mamou | G06Q 10/10 |
| | | | 702/19 |
| 2006/0294578 A1 | 12/2006 | Burke | |
| 2008/0077570 A1* | 3/2008 | Tang | G06F 16/3346 |
| 2008/0219990 A1* | 9/2008 | Fanger | C07K 14/82 |
| | | | 424/139.1 |
| 2008/0319990 A1* | 12/2008 | Taranenko | G06F 16/29 |
| 2009/0024522 A1 | 1/2009 | Reunert | |
| 2009/0077070 A1* | 3/2009 | DiFilippo | G06F 16/2458 |
| 2009/0327450 A1 | 12/2009 | Alkove | |
| 2010/0030752 A1* | 2/2010 | Goldentouch | G06F 16/81 |
| | | | 707/797 |
| 2010/0106709 A1* | 4/2010 | Imai | G06F 21/6218 |
| | | | 707/713 |
| 2010/0174725 A1* | 7/2010 | Adams | G06F 16/242 |
| | | | 707/749 |
| 2010/0228699 A1* | 9/2010 | Webber | G06F 21/6245 |
| | | | 707/622 |
| 2010/0250285 A1* | 9/2010 | Shelton | G06F 21/6254 |
| | | | 705/3 |
| 2011/0030752 A1 | 2/2011 | Livacich | |
| 2011/0106821 A1* | 5/2011 | Hassanzadeh | G06F 16/367 |
| | | | 707/749 |

FOREIGN PATENT DOCUMENTS

| | | |
|---|---|---|
| WO | 2005/041100 A2 | 5/2005 |
| WO | WO 2005/041100 A2 * | 5/2005 |
| WO | WO2005041100 A2 * | 5/2005 |

OTHER PUBLICATIONS

International Search Report Issued in PCT/US2013/040005 dated Oct. 11, 2013 (6 pages total).
Written Opinion Issued in PCT/US2013/040005 dated Oct. 11, 2013 (9 pages total).
International Preliminary Report on Patentability Issued in PCT/US2013/040005 dated Oct. 11, 2013 (10 pages total).
Examination Report dated Apr. 29, 2020, issued in connection with corresponding EP Application No. 13 724 466.1 (4 pages total).

* cited by examiner

METHOD AND SYSTEM FOR SHARING ACCESS TO A DATABASE

RELATED APPLICATION

This application is a divisional of Ser. No. 14/399,421 filed Nov. 6, 2014, entitled, "Method and System for Sharing Access to a Database" which is a 371 of International Application No. PCT/US2013/040005, filed May 7, 2013, entitled, "Method and System for Sharing Access to a Database" which claims the benefit of U.S. Provisional Patent Application No. 61/164,898, filed on May 7, 2012, which are incorporated herein by reference in their entirety.

TECHNICAL FIELD

The subject matter described herein relates to a computer-implemented method and a system for sharing access to a database of records relating to clinical trial investigators amongst a number of users. It also relates to a computer program product residing on a non-transitory tangible storage medium for sharing access to a database of records relating to clinical trial investigators amongst a number of users.

BACKGROUND

An important part of the process of developing new medicines is the conduct of clinical trials. Pharmaceutical companies developing new medicines engage doctors with experience in clinical research, known as clinical trial investigators, to conduct these clinical trials under controlled conditions. The quality, cost and speed of a clinical trial will naturally be dependent upon the investigator selected to conduct it.

The selection of an appropriate clinical trial investigator is a complex matter. An investigator is often selected based on their particular clinical experience and also whether previous trials they have performed have been of adequate quality, cost-effective and carried out with reasonable speed. Pharmaceutical companies typically keep records of the clinical trial investigators that they have used in the past to help with this selection process. However, these records are proprietary and therefore each company's records are naturally limited in their scope, covering only those clinical trial investigators that the company has historically used.

SUMMARY

In accordance with a first aspect, there is provided a computer-implemented method for sharing access to a database of records relating to clinical trial investigators amongst a number of users, each record including a number of data fields associated with a clinical trial investigator and having associated metadata indicating a record owner.

The method comprises: a) receiving a database query from a first user; b) resolving the query using a first subset of the records in the database including only those records for which the associated metadata indicates that the record owner is the first user and those records for which the associated metadata indicates that the record owner is another user which has registered a sharing rule in respect of the first user, whereby the first user is granted permission to access its records; and c) generating a result set including only those records used to resolve the query that satisfy the query.

By allowing users (i.e. pharmaceutical companies) to access information on clinical trial investigators owned by many different users (i.e. different pharmaceutical companies), pharmaceutical companies are able to select clinical trial investigators from a wider pool than comprised in their own records. They are therefore able to select an investigator that is not covered by their own records but is in another company's records or access more information about an investigator that they have used before. The selection process is therefore significantly enhanced and the difficulties previously faced, i.e. that companies could only base the selection on their own historical data, are overcome. This enables pharmaceutical companies to make better predictions of project timelines and improve resource allocation. At the same time, the companies are able to retain control of their own data; the sharing rules are registered by the users. As an example of the result provided by the invention, Company A can share their records with Company B, and Company B can share their records with Company C, but Company A can choose not to share their records with Company C. Equally, Company A can choose to remove themselves from the sharing without having lost long term control of their data.

Furthermore, investigators will be encouraged to compete on quality, speed and cost since excellent performance on a clinical trial for one company will be visible to other companies, potentially increasing the number of research opportunities that they would be offered in the future.

The database of records may be a single database comprising all of the records (i.e. a unified database) or it may be a number of separate databases throughout which the records are distributed. The database query is preferably a Structured Query Language (SQL) query, and is preferably received over a computer network.

The sharing rule is preferably stored in a database table. The database table may form part of the same database that comprises the database of records. The sharing rule is preferably registered by the other user by causing an identifier for the first user to be stored in a row of the table indexable by an identifier of the first user. The result set may be transmitted over a computer network to the first user.

The method may further comprise excluding records relating to clinical trial investigators in a set of opted-out investigators from the first subset of records. The set of opted-out investigators will usually be stored in a table in a database. The set of opted-out investigators indicates those investigators that have expressed a preference that records relating to them are not accessible. It may be necessary to allow investigators to opt out for compliance with data protection laws in some countries.

However, the method typically further comprises excluding all records from the first subset of records except those records relating to clinical trial investigators in a set of opted-in investigators. The set of opted-in investigators will usually be stored in a table in a database. The set of opted-in investigators indicates those investigators that have expressed a preference that records relating to them are accessible. It may be necessary to ensure that investigators have actively opted in before allowing access to records relating to them for compliance with data protection laws in some countries.

In a first embodiment, the method further comprises restricting the first subset of records used to resolve the query based on a volume rule registered by the other user in respect of the first user, the volume rule specifying a predetermined number of records in the database, for which the associated metadata indicates that the record owner is the other user, that the first user may access by the query.

In a second embodiment, the method further comprises restricting the first subset of records used to resolve the query based on a volume rule registered by the other user in respect of the first user, the volume rule specifying a predetermined number of records in the database, for which the associated metadata indicates that the record owner is the other user, that the first user may access in a predetermined period of time.

In a third embodiment, the method further comprises restricting the first subset of records used to resolve the query based on a volume rule registered by the other user in respect of the first user, the volume rule specifying a number of records, for which the associated metadata indicates that the record owner is the other user, that the first user may access based on a function of a predetermined number of records in the database, for which the associated metadata indicates that the record owner is the first user, that the other user may access by the query specified in a volume rule registered by the first user in respect of the other user.

The volume rule or volume rules are typically stored in a database table. The database table may form part of the same database that comprises the database of records.

The method may further comprise restricting the fields that are present in each record of the result set in accordance with a field restriction rule registered by the other user in respect of the first user.

The field restriction rule is typically stored in a database table. The database table may form part of the same database that comprises the database of records.

In a preferred embodiment, in step (b), the query may be resolved using a second subset of records in the database in addition to the first subset, the second subset of records including only those records for which the associated metadata indicates that the record owner is a clinical trial investigator identified in the query.

One of the data fields in each record can be a unique identifier having a value corresponding to the clinical trial investigator associated with the data fields of the record.

In accordance with a second aspect, there is provided a system for sharing access to a database of records relating to clinical trial investigators amongst a number of users, the system comprising one or more processors; a data store coupled to and readable by the or each processor, the data store having stored therein a database of records relating to clinical trial investigators, each record including a number of data fields associated with a clinical trial investigator and having associated metadata indicating a record owner; and a memory coupled to and readable by the or each processor, the memory having stored therein instructions, which when executed by the or each processor cause the or each processor to carry out a method according to the first aspect of the invention.

In accordance with a third aspect, there is provided a computer program product residing on a non-transitory tangible storage medium for sharing access to a database of records relating to clinical trial investigators amongst a number of users, each record including a number of data fields associated with a clinical trial investigator and having associated metadata indicating a record owner, the computer program product comprising processor-readable instructions configured to cause one or more processors to carry out a method according to the first aspect of the invention.

In accordance with a fourth aspect, there is provided a computer-implemented method for matching data representing contact details to a master list of contact details for a set of individuals identified by the contact details, the method comprising: a) receiving name data specifying a name; b) applying a phonetic algorithm to the name to generate a phonetic representation of the name; c) generating a commonality index for the name; d) generating a name matching score by comparing the phonetic representation of the name with a name forming part of each entry in the master list, the name matching score indicating the similarity between the phonetic representation and the name forming part of each entry; e) weighting the name matching score by a name weighting coefficient that is inversely proportional to the commonality index; and f) comparing an overall score generated from the weighted name matching score with a predetermined threshold and indicating a match if the threshold is exceeded.

The above method enables an individual to be correctly identified by incomplete or incorrect name data. This is beneficial for use with the method of the first aspect because the records relating to clinical trial investigators can identify the investigators by a unique identifier. A user can then search the master list by name, which can result in a match even if the name they have entered is incomplete or incorrect. A match can be used to return the unique identifier, which can then in turn be used in a query of the database of records relating to clinical trial investigators referred to with reference to the first aspect.

The method may further comprise retrieving a name root for a part of the name data representing a given name from a database table linking name roots to modified forms of the given name. This enables nicknames to be entered by users, the method seamlessly replacing them with the full name. For example, the database table may link "Dave" with "David" and "Rob" with "Robert".

In some implementations, the commonality index is only generated for a part of the name data representing a surname. In a preferred implementation, the phonetic algorithm is Metaphone. In one implementation, the method further comprises receiving address data specifying an address; obtaining location co-ordinates for the address; generating a location matching score by comparing the location co-ordinates with the location of an address forming part of each entry in the master list, the location matching score indicating the proximity of the location co-ordinates to the address forming part of each entry; weighting the location matching score by a location weighting coefficient; and generating the overall score from the weighted location and name matching scores. This expands the method so that matching can be performed based on location as well as name.

In a second implementation, the method further comprises: receiving occupation data specifying an occupation; generating an occupation matching score by comparing the occupation with an occupation forming part of each entry in the master list, the occupation matching score indicating the similarity between the occupation and the occupation forming part of each entry; weighting the occupation matching score by an occupation matching coefficient; and generating the overall score from the weighted occupation and name matching scores. This expands the method so that matching can be performed based on occupation as well as location and/or name.

The method may further comprise returning a unique identifier for an individual in the master list in the event of a name match and/or a location match and/or an occupation match.

In accordance with a fifth aspect, there is provided a system for matching data representing contact details to a master list of contact details for a set of individuals identified by the contact details, the system comprising one or more processors, and a memory coupled to and readable by the or each processor, the memory having stored therein instructions, which when executed by the or each processor cause the or each processor to carry out a method according to the fourth aspect of the invention.

In accordance with a sixth aspect, there is provided a computer program product residing on a non-transitory tangible storage medium for matching data representing contact details to a master list of contact details for a set of individuals identified by the contact details, the computer program product comprising processor-readable instructions configured to cause one or more processors to carry out a method according to the fourth aspect of the invention.

In accordance with a seventh aspect, there is provided a computer-implemented method for accessing a database of records relating to clinical trial investigators, each record including a number of data fields associated with a clinical trial investigator and having associated metadata indicating a record owner, wherein the method comprises: a) receiving a database query from a first user; b) determining whether the user is a clinical trial investigator; c) if the user is a clinical trial investigator, resolving the query using a first subset of the records in the database including each record associated with the clinical trial investigator, irrespective of the record owner indicated by the associated metadata; and d) generating a result set including only those records used to resolve the query that satisfy the query. This provides a mechanism for a clinical trial investigator to review all of the records relating to him, irrespective of the ownership of those records.

In accordance with an eighth aspect, there is provided a system for accessing a database of records relating to clinical trial investigators, the system comprising one or more processors; a data store coupled to and readable by the or each processor, the data store having stored therein a database of records relating to clinical trial investigators, each record including a number of data fields associated with a clinical trial investigator and having associated metadata indicating a record owner; and a memory coupled to and readable by the or each processor, the memory having stored therein instructions, which when executed by the or each processor cause the or each processor to carry out a method according to the seventh aspect of the invention.

In accordance with an ninth aspect, there is provided a computer program product residing on a non-transitory tangible storage medium for accessing a database of records relating to clinical trial investigators, each record including a number of data fields associated with a clinical trial investigator and having associated metadata indicating a record owner, the computer program product comprising processor-readable instructions configured to cause one or more processors to carry out a method according to the seventh aspect of the invention.

Implementations of the current subject matter can include, but are not limited to, systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
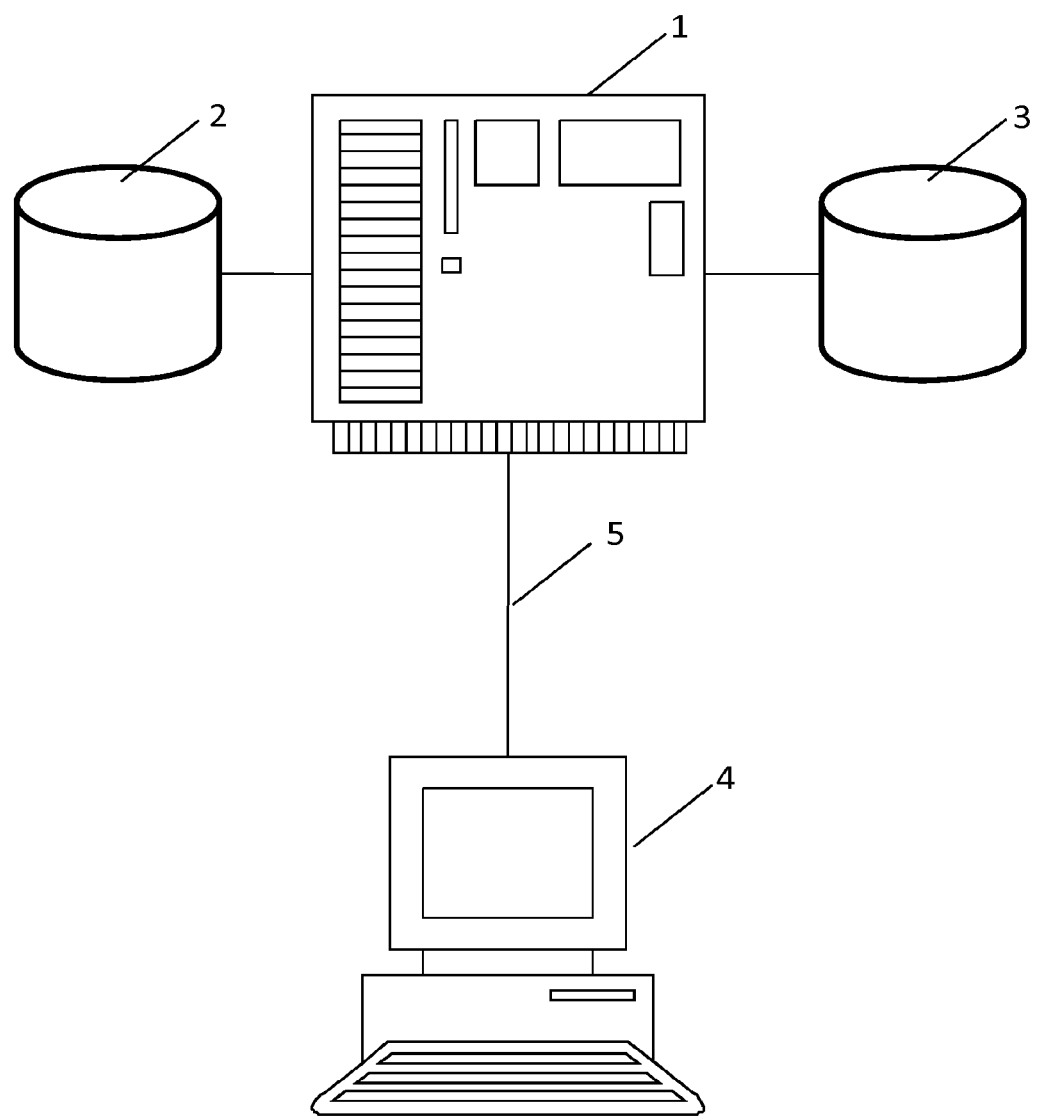
FIG. 1 shows a computer system adapted to perform the methods shown in the flowcharts of FIGS. 2 to 4.

FIG. 1 shows a computer system suitable for performing the methods and algorithms described below with reference to FIGS. 2 to 4. It comprises a database server 1 hosting a SQL database, such as PostrgreSQL, MySQL, Oracle or similar. Although only one server 1 is shown, it should be realised that in a practical implementation, there may be several servers operating together to handle queries where high demand or failsafe redundant operation is required. Those skilled in the art will be aware how to arrange multiple servers to ensure load balancing between multiple servers and failover.

The database server 1 is coupled to a persistent storage volume 2, which may be direct attached storage or a networked storage solution, such as a volume accessible over a storage area network. The volume 2 stores the programs required by the system to operate, such as the operating system and the SQL database itself.

Another persistent storage volume 3 is also coupled to the database server 1. This stores a database of records relating to clinical trial investigators. The volume 3 may be a partition on the same storage device as that which volume 2 resides on. However, this would be unusual. Typically, volume 3 will be a large volume accessible over a storage area network. It will typically make use of redundant storage technology such as RAID (Redundant Array of Inexpensive Disks) to ensure availability of the data in the event of one or more storage device failures.

The database server 1 is able to receive queries from a user at a remote terminal 4 over a computer network 5, resolve those queries using the database of records on volume 3 and then return a set of results to the remote terminal 4 over computer network 5. There may of course be many users, each of which is able to send queries to the database server 1. The computer network 5 will typically be, at least in part, the Internet.

The database of records is arranged as a set of virtual private databases (VPDs), each comprising the records relating to clinical trial investigators that are owned by one pharmaceutical company, contract research organisation, regulator, or other organisation. Each record includes a number of data fields associated with a clinical trial investigator (for example, their name and address, and details of research programmes they have carried out) and has associated metadata indicating a record owner. By way of this metadata, the database can ensure that only the owner or other permitted users can access the record. Application software that handles the received queries along with the database controls which other users are permitted to access a record using sharing rules as will be described below.

Figure 2:
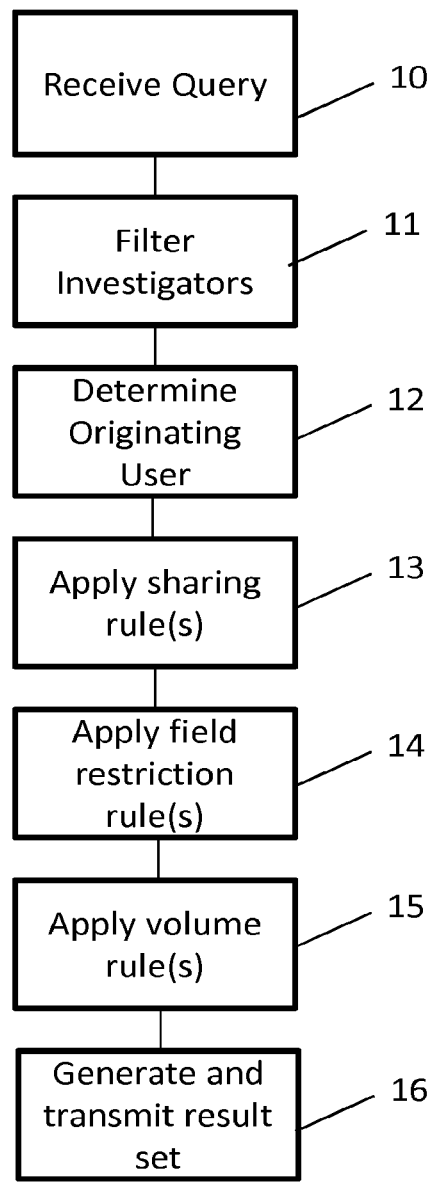
FIG. 2 shows a flowchart of a method according to one embodiment.

FIG. 2 illustrates the algorithm employed to allow pharmaceutical companies and other organisations to pool their information relating to clinical trial investigators. By way of this algorithm, a search query from one pharmaceutical company can be resolved using not only their own data but also that from other companies that have agreed to share their data with the company from which the query originates.

The algorithm will be carried out by the application software mentioned above. It starts in step 10 when a query is received by the database server 1 over a computer network 2 from a remote terminal 3, where the query is entered by a user. The query will usually be a SQL query, although it may be presented in another form at the terminal and translated by an application programming interface to SQL.

After the query is received, the next step 11 is to filter the records in the database to include only those records relating to clinical trial investigators who have granted permission for their details to appear in the results of queries. Such permission may be granted either by investigators opting in or by investigators opting out. Opting in or out may be achieved by selecting a hyperlink, which points to a web application running on a web server coupled to the database server 1. When investigators are required to opt in to be included, selecting the hyperlink will cause the web application to instruct the database server 1 to update a database table of opted-in investigators in the database. On the other hand, when investigators are required to opt out to be excluded, selecting the hyperlink will cause the web application to instruct the database server 1 to update a database table of opted-out investigators in the database.

In the case of opting in, filtered versions of the virtual private databases will be created containing only those investigators whose unique identifier is present in the database table of opted-in investigators. In the case of opting out, filtered versions of each of the virtual private databases will be created containing all investigators except those whose unique identifier is present in the database table of opted-out investigators.

In step 12, the application software determines which user the query originated from. The users are normally identified by a unique username or identification number or alphanumerical sequence. The identity of the user identified in step 12 is then used in step 13 to apply any appropriate sharing rule or rules. The sharing rule or rules identifies other users with which the originating user has chosen to share their data on clinical trial investigators. Thus, the sharing rules effectively link the virtual private databases belonging to different organisations. For example, organisations A and B may agree to share their data, organisations A and C may agree to share their data, whilst organisations B and C do not. Therefore, there will be sharing rules registered by organisation A in respect of organisations B and C and by organisations B and C in respect of organisation A. Neither of organisations B and C will register a sharing rule in respect of the other. When organisation A queries the database, the query will be resolved against a virtual merge of the records in the database owned by organisations A, B and C. When organisation B queries the database, the query will be resolved against a virtual merge of the records in the database owned by organisations B and A, but not C. Similarly, when organisation C queries the database, the query will be resolved against a virtual merge of the records in the database owned by organisations C and A, but not B.

The sharing rules are stored in a table in the database. Each row is indexed by the unique identifier of the users. Other columns in the row than the index store the identifiers of other users for who the indexed user has registered a sharing rule. Thus, the table can be searched using the index by the unique user identifier for the originating user determined in step 12 to see which other users the originating user has registered a sharing rule with. The sharing rules may be registered using a web application running on a web server coupled to the database server. The web application will allow each user, after entering appropriate login credentials, to select other users that they wish to share their data with and then instruct the database server 1 to update the database table of sharing rules accordingly.

To apply the sharing rules in step 13, the sharing rules for the originating user determined in step 12 are retrieved from the database table of sharing rules. This identifies the other users in respect of which the originating user has registered sharing rules. The application then forms a view including only those of the filtered virtual private databases that the originating user is entitled to access by virtue of the retrieved sharing rules.

The next step 14 in the algorithm is to apply any field restriction rules. The field restriction rules are not obligatory, but may be invoked by a user if desired. They restrict the records belonging to a particular user that the user originating the query is able to see based on the value of a field in the records. For example, a field restriction rule may prevent the originating user from accessing records belonging to another user that relate to clinical trial investigators specialising in oncology. The other user may wish to register this field restriction rule if the originating user has not shared any records which relate to clinical trial investigators specialising in oncology. In another example, a field restriction rule may only allow the originating user to access records belonging to another user that relate to clinical trial investigators specialising in cardiology. The other user may wish to register this field restriction rule if the originating user has only shared records which relate to clinical trial investigators specialising in cardiology.

The field restriction rules are again stored in a table in the database. Each rule is indexed by the originating user against which it should be applied and specifies the user to whom it belongs (i.e. to whose records it should be applied) and the field and its associated value on which the restriction is to be based. It also specifies how the restriction is to be applied, i.e. whether all records other than those having a field with the associated value are to be excluded or whether only those records having a field with the associated value are to be included. The application then forms a second view from the view output from step 13 in which the records are restricted in accordance with the field restriction rule or rules applied.

The next stage is the application of volume rules in step 15. Volume rules are used to restrict the number of records that an originating user can access. For example, an originating user may be prevented from accessing more than 100 records because it has only shared 100 of its own records. The restriction may be based on an absolute number of records or a function of the number of records that the originating user has shared or an absolute number of records that are accessible in a given period of time.

The volume rules are stored in a table in the database. Each rule is indexed by the originating user against which it should be applied and specifies the user to whom it belongs (i.e. to whose records it should be applied) and the nature of the volume rule. This could specify an absolute number of records which may be accessed, a given time period within which the absolute number of records may be accessed or a function (typically a multiple) of the number of records that the originating user has shared. The application forms a third view from the second view of step 14 in which the records are restricted in accordance with the volume rule or rules applied.

This third view is effectively a merged set of records which the originating user is entitled to access (i.e. their own and other user's records for which a sharing rule has been registered) that is restricted in accordance with any field restriction and volume rules. The SQL query received in step 10 may be resolved against this third view to generate a result set of records from the third view that satisfy the conditions of the query. This result set is generated in step 16 and then transmitted back to the originating user's terminal 4 over the computer network 5.

In some implementations, the third view may also comprise records for which the associated metadata indicates that the record owner is a clinical trial investigator identified in the query. This ensures that data provided to the database by clinical trial investigators themselves is automatically shared without an explicit sharing rule being required. Thus, any queries conducted for a specific investigator will automatically return data supplied by the investigator alongside other data provided for that investigator by other organisations. Records provided by clinical trial investigators will usually be stored in a dedicated virtual private database.

Figure 3:
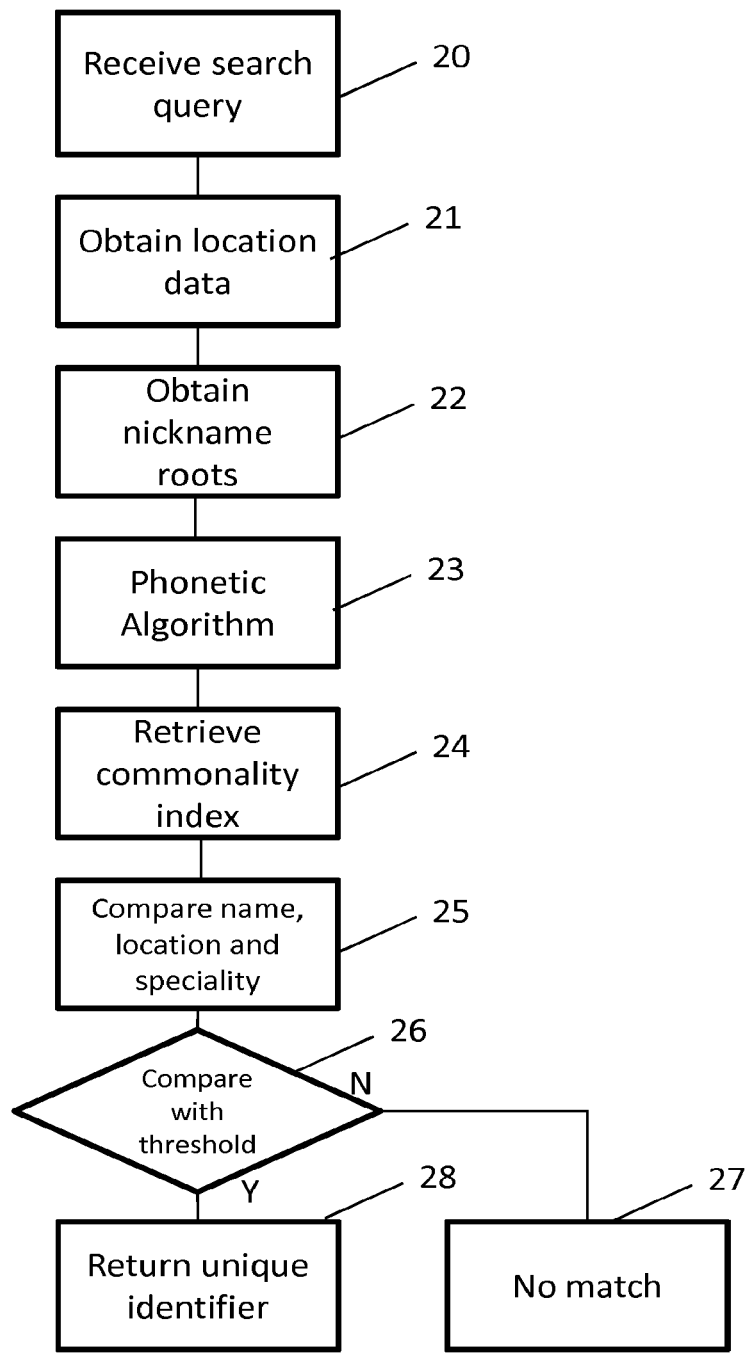
FIG. 3 shows a flowchart of a matching algorithm for use with the embodiment of FIG. 2.

FIG. 3 illustrates a matching algorithm. The matching algorithm allows a unique identifier for a clinical trial investigator to be found based on a search query for that investigator even when the details of the investigator provided are incomplete or incorrect. The unique identifier is required for retrieving data relating to a particular clinical trial investigator in the method of FIG. 2 because the database indexes the records using the unique identifier. This links the investigators across different virtual private databases within the database so that there is no chance that a record relating to an investigator is not returned, which could be the case if the investigator's name were used to index the records and the name were incomplete or incorrect. It also reduces the chance of confusion between similarly named investigators.

The algorithm starts in step 20 on receipt of a search query by the database server 1 over computer network 5. This query specifies contact details for the investigator being searched, such as the given name, surname, address and speciality or occupation. In step 21, latitude and longitude co-ordinates for the address provided in the query are obtained.

In step 22, a database of name roots is searched using the given name. The database of name roots links nicknames and short forms of name with the corresponding complete or formal name, which is returned from the search. This ensures that if a nickname or short form of name is provided in the search query, it is automatically replaced with the complete or formal name.

In step 23, the Metaphone phonetic algorithm is run on the complete or formal name returned from step 22 and the surname provided in the query. A phonetic algorithm is an algorithm for indexing of words by their pronunciation. It is useful because it can prevent accidental misspelling of names from being important. Thus, there is no distinction between the Metaphone code for "Clare" and "Claire", for example.

Next, in step 24, a commonality index is retrieved for the surname from a database table, which links surnames to a corresponding value of commonality index. The commonality index provides an indication of how common a surname is. If the surname is not in the database table then a commonality index of zero is assumed.

Then in step 25, the latitude and longitude co-ordinates from step 21, Metaphone code from step 23 and speciality data from the query received in step 20 are compared with corresponding fields for each entry in a master table of investigators.

The proximity of the latitude and longitude co-ordinates to those for each entry in the master table is determined. A closer proximity generates a higher proximity score. The Metaphone code is compared for similarity to the codes for each entry in the master table. A higher similarity will generate a higher name score. The speciality data is compared with speciality fields for each entry in the master table. A higher similarity will generate a higher speciality score.

For each entry in the master list, weighted versions of each of the proximity, name and speciality scores and then added together and compared with a threshold in step 26. The proximity and speciality scores are simply weighted by respective constant coefficients. The name score is weighted by a coefficient that is inversely proportional to the commonality index. This means that a more common name must be more closely matched to generate a positive result. If the threshold is not exceeded then, in step 27, no match is indicated. If on the other hand, the threshold is exceeded then, in step 28, the unique identifier for the matched entry in the master list is returned to the user who made the query in step 20.

Figure 4:
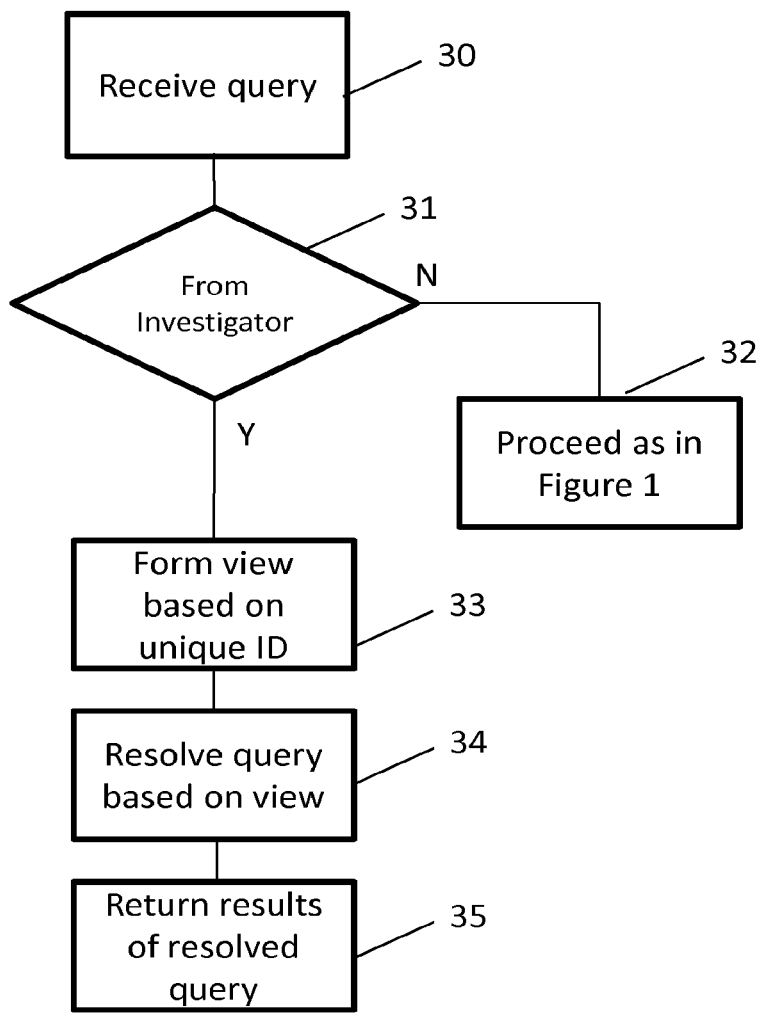
FIG. 4 shows a flowchart of a method performed in handling a query received from a clinical trial investigator.

FIG. 4 shows a method that is performed in handling a query received by a clinical trial investigator. The method starts in step 30 with the receipt of a query by the database server 1 over the computer network 5. In step 31, it is determined whether the identity of the user from which the query originated is a clinical trial investigator, for example by comparing their username or identity with a list of known clinical trial investigators. If the user is not a clinical trial investigator, then in step 32 the method finishes and the query may be handled normally as shown with reference to FIG. 2.

If the user who originated the query is determined to be a clinical trial investigator then in step 33, a view of all the records in the database (i.e. in all of the virtual private databases) that relate to the clinical trial investigator who initiated the query is formed. Whether a record relates to the particular clinical trial investigator can be determined using their unique user identifier, which will form part of each record. The view thus formed includes only those records relating to the clinical trial investigator who initiated the query.

The query can then be resolved in step 34 based on this view to generate a result set including only those records in the view that satisfy the query. The result set is then returned in step 35 over the computer network 5 to the originating clinical trial investigator.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for matching separate contact details to a master list of contact details for a plurality of individuals identified by the contact details in the master list, the method comprising steps of:

receiving one or more separate contact details comprising a name;

generating by a computing device including a hardware processor, a phonetic representation of the name, a commonality index for the name, a name matching score indicating similarity between the phonetic representation and the name forming part of the separate contact details in each entry of the master list, and an overall score of the name matching score of all of one or more separate contact details, wherein location information in relation to the name and phonetic information in relation to the name are compared by the hardware processor to corresponding information in the master list, and wherein a proximity score and the name matching score are generated by the hardware processor based on the comparison of the location information and phonetic information to the corresponding information within the master list, wherein a unique client identifier is identified by comparing the location information and the phonetic information to the master list;

weighting the name matching score by a name weighting coefficient that is inversely proportional to the generated commonality index; and comparing the overall score with a predetermined threshold and indicating, wherein a match exists when the threshold is exceeded, wherein the one or more separate contact details comprise an address further comprising steps of:

obtaining location co-ordinates for the address;

generating a location matching score;

weighting the locating matching score by a location weighting coefficient; and generating the overall score from the weighted location and name matching scores.

2. The method of claim 1, further comprising a step of retrieving a name root for a part of the name representing a given name from a table linking name roots to modified forms of the given name.

3. The method of claim 1, wherein the commonality index is generated only for a part of the name representing a surname.

4. The method of claim 1, wherein the generating is performed by a phonetic algorithm.

5. The method of claim 1, wherein the one or more separate contact details comprise an occupation and further comprising steps of:
generating an occupation matching score;
weighting the occupation matching score by an occupation matching coefficient; and
generating the overall score from the weighted occupation and name matching scores.

6. The method of claim 1, wherein the phonetic representation of the name is generated using a phonetic algorithm.

7. The method of claim 6, wherein the phonetic algorithm is Metaphone.

8. The method of claim 1, wherein the name matching score is generated by comparing the phonetic representation of the name with a name forming part of each entry in the master list.

9. The method of claim 1, wherein a location matching score is generated by comparing a set of location co-ordinates to a location in each entry in the master list.

10. The method of claim 1, wherein a speciality score is generated by comparing speciality data to speciality fields in each entry in the master list.

11. The method of claim 1, wherein the hardware processor compares occupational data in relation to the name to the corresponding information in the master list, and generates an occupational score based on the comparison.

12. A system for matching separate contact details to a master list of contact details for a plurality of individuals identified by the contact details in the master list, the system comprising:
a computing device including a hardware processor configured to:
receive one or more separate contact details comprising a name;
generate by the hardware processor a phonetic representation of the name a commonality index for the name, a name matching score indicating similarity between the phonetic representation and the name forming part of the separate contact details in each entry of the master list, and an overall score of the name matching score of all of one or more separate contact details, wherein location information in relation to the name and phonetic information in relation to the name are compared by the hardware processor to corresponding information in the master list, and wherein a proximity score and the name matching score are generated by the hardware processor based on the comparison of the location information and phonetic information to the corresponding information within the master list, wherein a unique client identifier is identified by comparing the location information and the phonetic information to the master list;
weigh the name matching score by a name weighting coefficient that is inversely proportional to the generated commonality index; and
compare the overall score with a predetermined threshold and indicating,
wherein a match exists when the threshold is exceeded, wherein the one or more separate contact details comprise and the one or more processors are further configured to:
obtain location co-ordinates for the address;
generate a location matching score indicating the proximity of the location co-ordinates to the address forming part of the separate contact details in each entry of the master list;
weigh the location matching score by a location weighting coefficient; and
generate the overall score from the weighted location and name matching scores.

13. The system of claim 12, wherein the one or more processors are further configured to retrieve a name root for a part of the name representing a given name from a table linking name roots to modified forms of the given name.

14. The system of claim 12, wherein the commonality index is generated only for a part of the name representing a surname.

15. The system of claim 12, wherein the one or more processors perform the generating by executing a phonetic algorithm.

16. The system of claim 12, wherein the one or more separate contact details comprise an occupation and the one or more processors are further configured to:
generate an occupation matching score indicating the similarity between the occupation and the occupation forming part of the separate contact details in each entry of the master list;
weigh the occupation matching score by an occupation matching coefficient; and
generate the overall score from the weighted occupation and name matching scores.

17. A computer program product residing on a non-transitory tangible storage medium for matching data representing contact details to a master list of contact details for a set of individuals identified by the contact details, the computer program product comprising processor-readable instructions configured to cause one or more processors to carry out a method for matching separate contact details to a master list of contact details for a plurality of individuals identified by the contact details in the master list, the method comprising steps of:
receiving one or more separate contact details comprising a name;
generating by a computing device including a hardware processor, a phonetic representation of the name a commonality index for the name, a name matching score indicating similarity between the phonetic representation and the name forming part of the separate contact details in each entry of the master list, and an overall score of the name matching score of all of one or more separate contact details, wherein location information in relation to the name and phonetic information in relation to the name are compared by the hardware processor to corresponding information in the master list, and wherein a proximity score and the name matching score are generated by the hardware processor based on the comparison of the location information and phonetic information to the corresponding information within the master list, wherein a unique client identifier is identified by comparing the location information and the phonetic information to the master list;
weighting the name matching score by a name weighting coefficient that is inversely proportional to the generated commonality index; and comparing the overall score with a predetermined threshold and indicating, wherein a match exists when the threshold is exceeded, wherein the one or more separate contact details comprise an address and further comprises steps of:

obtaining location co-ordinates for the address;

generating a location matching score indicating the proximity of the location co-ordinates to the address forming part of the separate contact details in each entry of the master list;

weighing the location matching score by a location weighting coefficient; and generating the overall score from the weighted location and name matching scores.

18. The computer program product of claim 17, wherein the one or more separate contact details comprise an occupation and further comprising steps of:

generating an occupation matching score indicating the similarity between the occupation and the occupation forming part of the separate contact details in each entry of the master list;

weighting the occupation matching score by an occupation matching coefficient; and generating the overall score from the weighted occupation and name matching scores.

* * * * *